United States Patent [19]
Bysouth et al.

[11] Patent Number: 5,801,820
[45] Date of Patent: Sep. 1, 1998

[54] FLOW-INJECTION GRADIENT DILUTION FOR OBTAINING UV SPECTRA OF CONCENTRATED SOLUTIONS

[75] Inventors: Stephen Robert Bysouth; Victor Pak-Ling Tong, both of Houston, Tex.

[73] Assignee: Shell Oil Company, Houston, Tex.

[21] Appl. No.: 618,181

[22] Filed: Mar. 19, 1996

[51] Int. Cl.$^6$ ................................................ G01N 1/00
[52] U.S. Cl. ........................................................ 356/36
[58] Field of Search ................. 356/36, 326; 73/864.12, 73/864.21, 864.22, 863.01; 422/81

[56] References Cited

U.S. PATENT DOCUMENTS

| | | | |
|---|---|---|---|
| 4,441,374 | 4/1984 | Suzuki | 73/864.12 |
| 4,794,806 | 1/1989 | Nicoli et al. | 73/863.01 |
| 4,950,397 | 8/1990 | Oquendo et al. | 422/81 X |

OTHER PUBLICATIONS

Tyson et al; "Flow Injection . . . Spectrometry", Analytic Chimica Acta, 145 1983 pp. 159–168.

Lazaro, F., Rios, A., Luque de Castro, M.D., and Valcarcel, Simultaneous Multiwavelength Detection in Flow Injection Analysis. Anal. Chim. Acta, 179 (1986), 279–287.

Gisin, M., and Thommen, C., Industrial Process Control by Flow Injection Analysis. Anal. Chim. Acta, 190 (1986), 165–176.

Toei, J., An Improved Zone Sampling Method for Flow Injection Analysis. Anal. Lett., 21 (1988), 1633–1651.

Souza, I. G., Bergamin F°, H., Krug, F. J., Nobrega, J. A., Oliveira, P.V., Reis, B. F., and Gine, M. F., On–line Electrolytic dissolution of alloys in Flow–Injection Analysis. Part 3. Multi–elemental Analysis of Stainless Steels by Inductively Coupled Plasma Atomic Emission Spectrometry. Anal. Chim. Acta, 245 (1991), 211–216.

Blanco, M., Coello, J., Iturriaga, H., Maspoch, S., Redon, M., and Riba, J., Multi–component Analysis of Concentrated Solutions by Flow–injection Analysis with Zone Sampling and Partial Least–squares Resolution. Anal. Chim., Acta, 259 (1992), 219–224.

Tyson, J. F., and Appleton, J.M.H., "A Continuous–Dilution Calibration Technique for Flame Atomic–Absorption Spectrophotometry," 9–14. 1983.

(List continued on next page.)

Primary Examiner—K. Hantis

[57] ABSTRACT

The invention relates to methods and apparatus for precise dilution of concentrated samples enabling their spectra to be obtained. The spectra thus obtained may then be used for calculation of the aromatic hydrocarbon content in the concentrated samples. This invention comprises an arrangement of computer-controlled pumps, an injection valve, a mixing chamber, a flow cell (these components are known as "the manifold") and a scanning spectrophotometer, with a sophisticated computational software program. The arrangement generates a reproducible, well-defined gradient from a concentrated sample which is continuously scanned and, using the computational software, allows the spectrum of the sample to be derived, even where the majority of the spectrum for the undiluted sample has an absorbance greater than the upper measurable limit of the spectrophotometer. All of the methods described in prior art publications differ from the present invention by their reliance on calibration (the adjustment of factors used, by comparing spectral data for a standard with its reference data) or characterization (measurement of the characteristics of the system, e.g., flowrate and mixing volume, and inclusion of these values in the calculation) of the systems for defining dilution factors, due to measurement of a single species/wavelength. The present invention requires no calibration/characterization for single species measurement since multiparameters (absorbance at many wavelengths) are monitored or conversely, can be used to obtain spectra of highly concentrated samples and therefore determine multiple species. None of the previous systems were used to obtain spectra per se.

10 Claims, 14 Drawing Sheets

OTHER PUBLICATIONS

Tyson, J.F., and Idris, A. B., "Flow Injection Sample Introduction for Atomic–absorption Spectrometry: Applications of a Simplified Model for Dispersion," Communication, *Analyst*, vol. 6, Oct. 1981, pp. 1125–1129.

Stewart, K. K., and Rosenfeld, A. G., Exponential Dilution Chambers for Scale Expansion in Flow Injection Analysis, Anal. Chem., 54 (1982), 2368–2372.

Ruzicka, J., and Hansen, H., Recent Developments in Flow Injection Analysis: Gradient Techniques and Hydrodynamic Injection. Anal. Chim. Acta, 145 (1983), 1–15.

Greenfield, S., Inductively Coupled Plasma–Atomic Emission Spectroscopy (ICP–AES) with Flow Injection Analysis (FIA). Spectrochim. Acta, 38B (1983), 93–105.

Lazaro, F., Rios, A., Luque de Castro, M.D., and Valcarcel, M., Diode Array Detectors in Hydrodynamic Analytical Systems. Analusis, 14 (1986), 378–388.

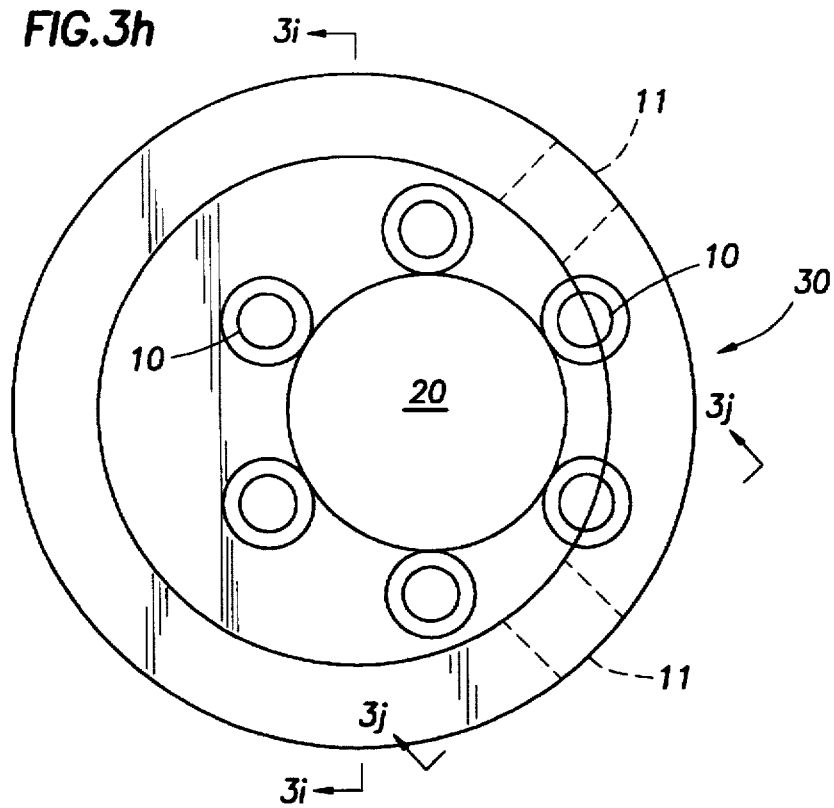
FIG.3h
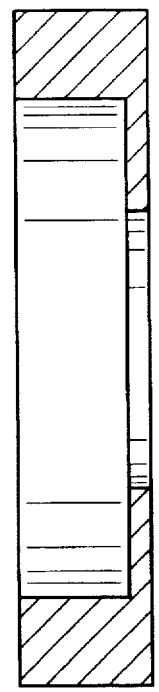
FIG.3i
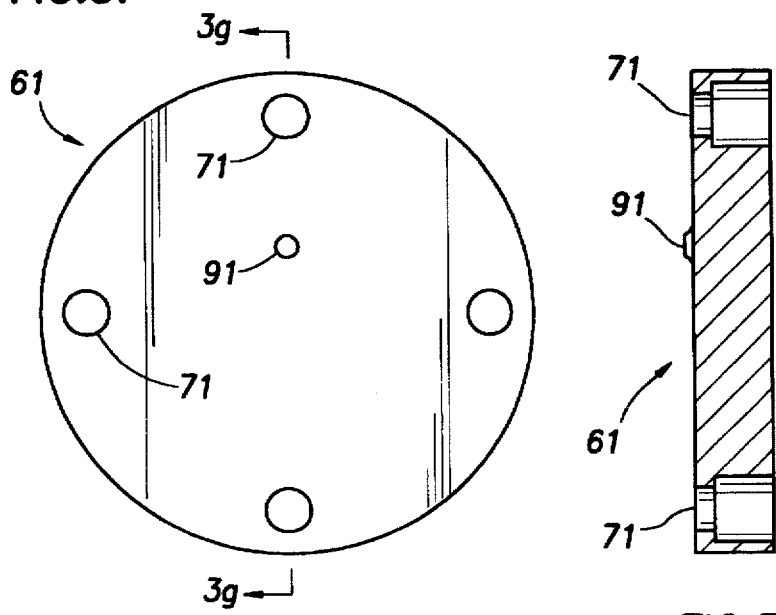
FIG.3f
FIG.3g
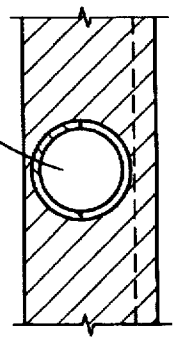
FIG.3j

FIG.5b
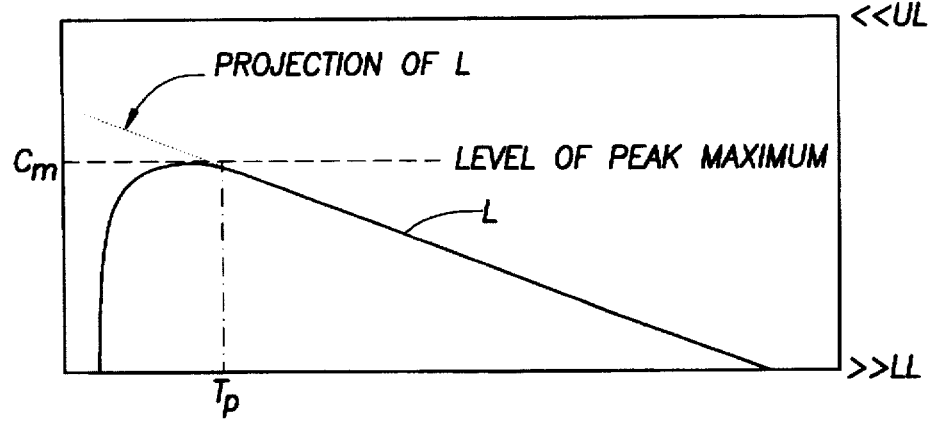
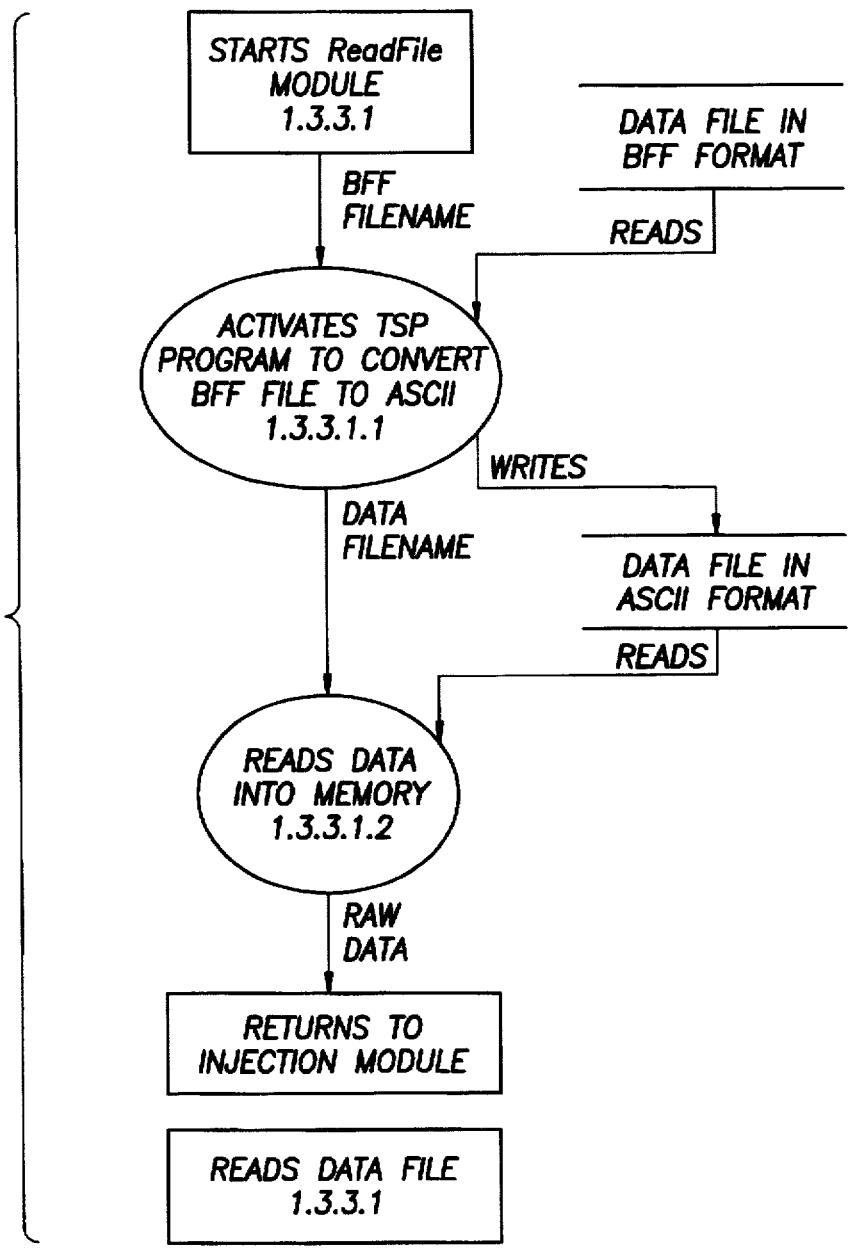
FIG.8e

FIG.6a

```
                AROMATIC DISTRIBUTION
INSTRUMENT TYPE : FOCUS/FIA        FILE DATE:1/20/96
SAMPLE NAME: QA 1801                SAMPLE#: 20B
WRC#: 123456                        MEAN      %rsd
ESTIMATED BENZENES=                 7.15      0.28
ESTIMATED NAPHTHALENES=             3.38      0.37
ESTIMATED PHENANTHRENES=            2.92      0.56
ESTIMATED CONDENSED TETRAAROMATICS= 3.09      0.27

ESTIMATED TOTAL AROMATICS (%wt arom)=16.54    0.34

PEAK WAVELENGTH:  200.0*  232.0   256.0*  266.0   286.0
PEAK INTENSITY:    54.07   29.03   13.80   12.32    8.11

CONCENTRATION=10.59   ZYMARK DATE:

DIAROMATIC INDEX 24.70              AROMATIC INDEX 19.50
```

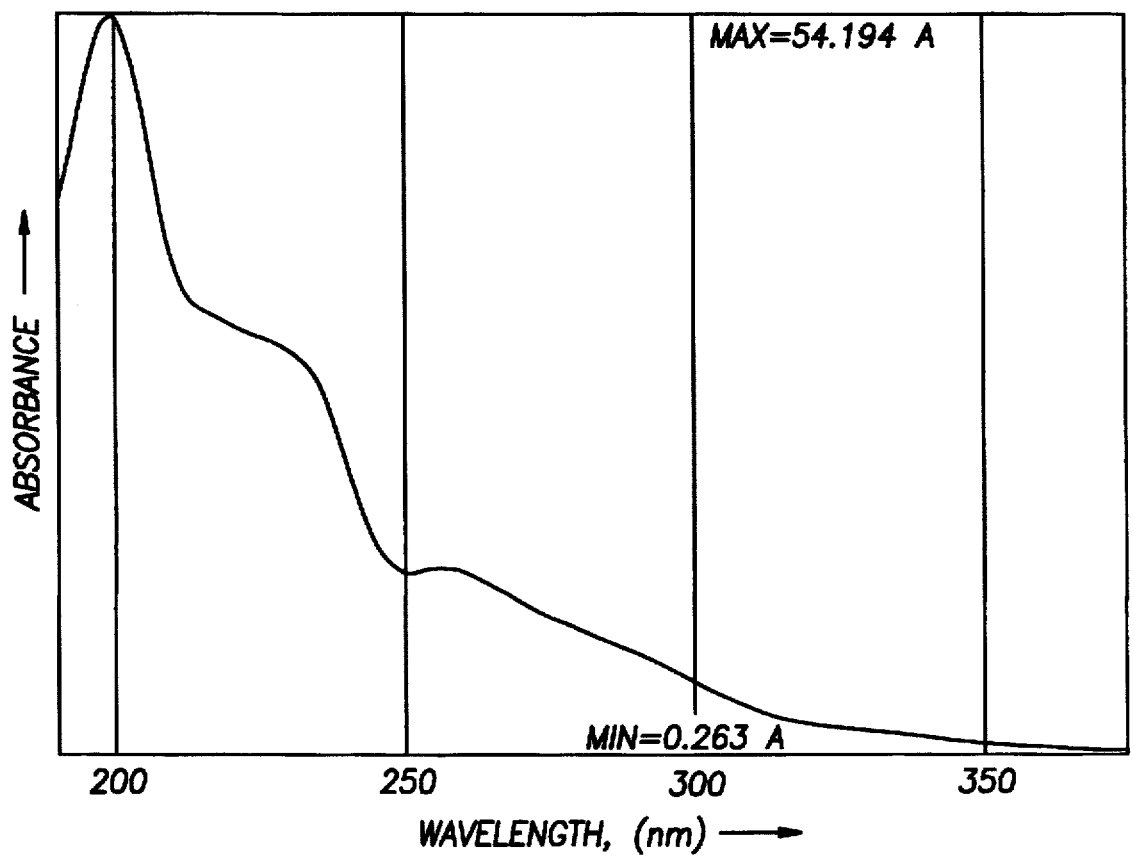

NORMALIZED ABSORBANCE SPECTRUM

FIG.6b

AROMATIC DISTRIBUTION

INSTRUMENT TYPE: LAMBDA 7
SAMPLE NAME: QA
WRC# 123456        SAMPLE# 1A
DATE RUN: NOV 15 1995

ESTIMATED BENZENES=            7.17
ESTIMATED NAPHTHALENES=        3.37
ESTIMATED PHENANTHRENES=       2.85
ESTIMATED CONDENSED TETRAAROMATICS=  3.00

ESTIMATED TOTAL AROMATICS=     16.40 %wt AROMATIC
AROMATIC INDEX=   19.35

TECHNICIAN: MBW     DISKETTE# 1100    FILENAME: S34561A.SP

| | | | | | |
|---|---|---|---|---|---|
| PEAK WAVELENGTH: | 200.2* | 232.2 | 256.3* | 266.3 | 286.3 nm |
| PEAK INTENSITY: | 0.6336 | 1.6059 | 0.7512 | 0.6734 | 0.4387 A |
| CONCENTRATION: | 0.1174 | 0.5564 | 0.5564 | 0.5564 | 0.556 g/l |
| INTENSITY(400nm): | 0.0054 A | | | | |

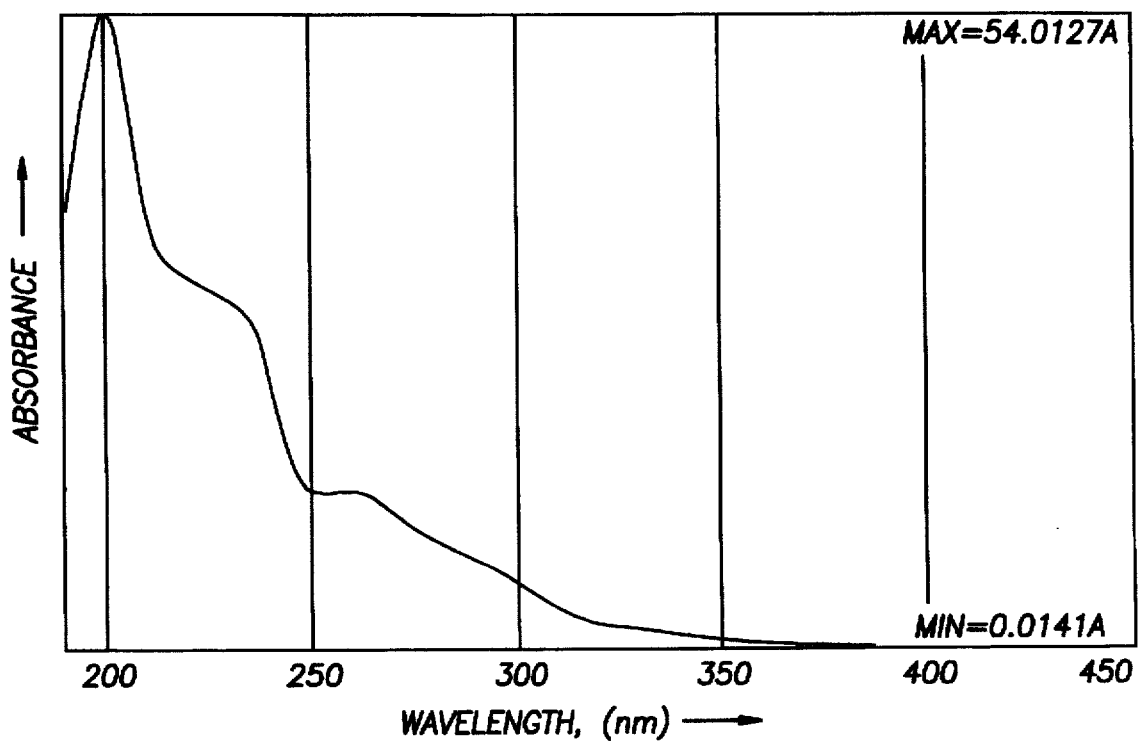

NORMALIZED ABSORBANCE SPECTRUM

FLOW-INJECTION GRADIENT DILUTION FOR OBTAINING UV SPECTRA OF CONCENTRATED SOLUTIONS

FIELD OF THE INVENTION

The invention relates to methods and apparatus for precise dilution of concentrated samples enabling their spectra to be obtained. The spectra thus obtained may then be used for calculation of the aromatic hydrocarbon content in the concentrated samples.

BACKGROUND OF THE INVENTION

Measurement of the levels of classes of aromatics in a hydrocarbon mixture has been carried out since the development of absorption spectrophotometers capable of making measurements at wavelengths down to 190 nm and shorter. These measurements were originally applied to feedstocks for lubricants but have been extended and modified to enable many materials to be analyzed. The method is based on determining the spectrum for the mixture over the wavelength range 190–365 nm and calculating the quantity of the various aromatic classes based on the absorbances at various regions of the spectrum. It is not intended here to examine the calculation method; however, all methods require some dilution of the samples and, in a laboratory analyzing a large range of types of unknowns, the degree of dilution needed to bring the absorbance across the spectrum on-range of a spectrophotometer is often unknown and, for some samples, the dilution required may be different for different regions of the spectrum when high precision is required. In order to overcome this problem, up to four fixed dilutions of the original material in duplicate were made (a total of eight solutions per sample). Additionally, optically pure decahydronaphthalein was used in combination with methylcyclohexane as the solvent, and this solvent mixture is expensive.

Although a robot may be used, the dilutions are very time consuming, taking about twelve hours for twenty samples, and use a significant volume of expensive, high-purity solvent. Once the sample has been diluted, these diluted samples must then be scanned and the spectra unified and results calculated, further increasing the time required to run a sample.

Alternatives were examined to see which had the greatest potential to both speed up the analysis and reduce solvent use. The alternatives examined were: (1) continue with the old method of dilution with updated equipment, (2) use a sophisticated diluting autosampler and (3) use flow-injection (FI) dilution. The latter (3) was selected since the others would either still require large volumes of solvent, or the technology, as required, was not available. Although the technology to perform accurate and precise FI dilutions was not available, development of such a system appeared to offer a number of advantages; for example, using a gradient allows the limited range of absorbances that can be measured (which defines the need for dilution) to be transformed onto the time domain, which is infinite. This would potentially allow infinite degrees of dilution.

The system developed requires little maintenance, uses considerably less solvent than the prior method and scans the solution as the dilution is made, increasing sample throughput per unit time.

SUMMARY OF THE INVENTION

This invention comprises an arrangement of computer-controlled pumps, an injection valve, a mixing chamber, a flow cell (these components are known as "the manifold") and a scanning spectrophotometer, with a sophisticated computational software program. The arrangement generates a reproducible, well-defined gradient from a concentrated sample which is continuously scanned and, using the computational software, allows the spectrum of the sample to be derived, even where the majority of the spectrum for the undiluted sample has an absorbance greater than the upper measurable limit of the spectrophotometer.

BRIEF DESCRIPTION OF THE DRAWINGS

FIG. 3b is an elevational view of the valve/mixer which replaces the tubing connector block of the valve of FIG. 3a.

FIG. 3f is a plan view of the base plate which attaches to the mixer block of FIG. 3d.

FIG. 3g is a sectional view taken along the line 3g—3g of FIG. 3f.

FIG. 3h is a plan view of the adapter that attaches the valve/mixer to the stirrer.

FIG. 3i is a sectional view taken along the line 3i—3i of FIG. 3h.

FIG. 3j is a view taken along line 3j—3j of FIG. 3h.

FIG. 5b shows how the start of the gradient $T_p$ is determined by intersecting line L with the level of peak maximum $C_m$.

FIG. 6a is a plot of three normalized absorbance spectra which are averaged to calculate aromatic content which is presented in the data at the top of FIG. 6a.

FIG. 6b is the same as FIG. 6a except the spectrum and data were obtained using serial dilution followed by scanning of these fixed dilutions (i.e., the prior dilution system) for comparison.

FIGS. 8a–e show data flow diagrams (i.e., showing what happens to the data in the process) for the computer programs used to practice the invention.

FIG. 8a shows data flow in the Main Module.

FIG. 8b shows data flow in the RunInfo Module.

FIG. 8c shows data flow in the Injection Module.

FIG. 8d shows data flow in the Determine $C_m$ Module.

FIG. 8e shows data flow in the ReadFile Module.

DESCRIPTION OF THE PREFERRED EMBODIMENTS

Figure 1:
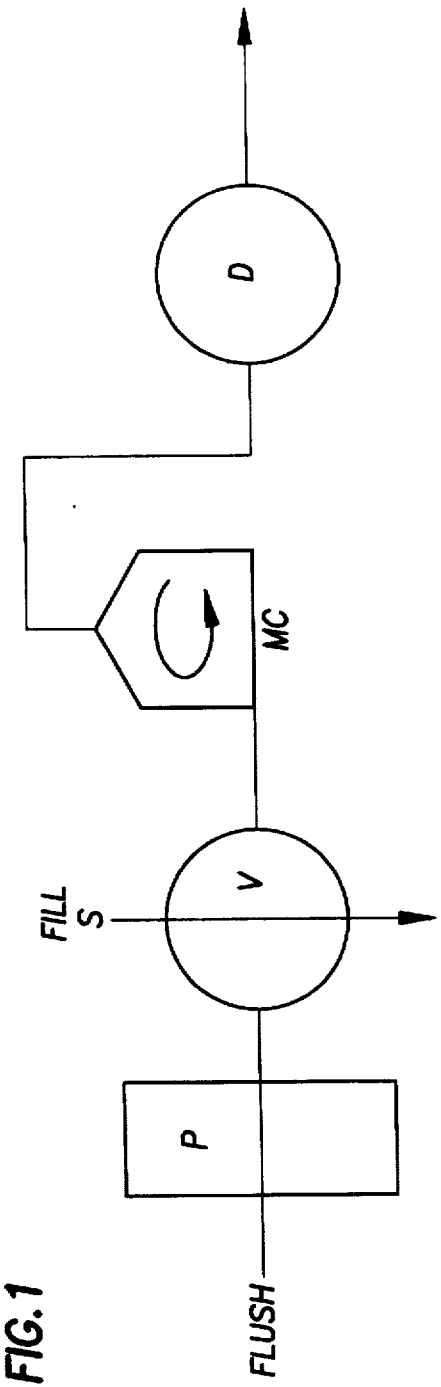
FIG. 1 is a simplified schematic of the flow injection system.

In FIG. 1, P is a pump which produces precise flows and pumps diluent through injection valve V. This valve contains a large volume sample loop or the mixing chamber MC in place of that loop. Both of the configurations where a large sample loop in the valve is followed by a mixing chamber and where the mixing chamber itself acts as the sample 'loop' have been demonstrated. There are, however, advantages to using the mixing chamber as the sample loop including the ability to isolate the mixer and allowing pure solvent to be viewed by the spectrophotometer while the chamber is filled at a faster rate. This is, therefore, the preferred embodiment. If an alternate gradient profile can be accommodated, use of a stirrer block in the mixing chamber may not be required. In that event, the mixer becomes an open tube. Once the sample S has entered the mixing chamber and the valve has been switched to the FLUSH position, the decrease in concentration as diluent flushes the sample out is monitored using either a photodiode array or a scanning spectrophotometer D.

Equipment

The basic "single well-stirred tank model" of mixing in a chamber, used by the instant invention, is well described in the chemical engineering text books and literature. Application of these equations and demonstration of mixing chamber dilution systems have been published by a number of authors. All of the methods described in known prior publications differ from the present invention by their reliance on calibration (the adjustment of factors used, by comparing data for a standard with its reference data) or characterization (measurement of the characteristics of the system, e.g., flowrate and mixing volume, and inclusion of these values in the calculation) of the systems for defining dilution factors, due to measurement of a single species/wavelength. The present invention requires no calibration/characterization for single species measurement since multiparameters (absorbance at many wavelengths) are monitored or conversely, can be used to obtain spectra of highly concentrated samples and therefore determine multiple species. None of these previous systems were used to obtain spectra per se.

Figure 2:
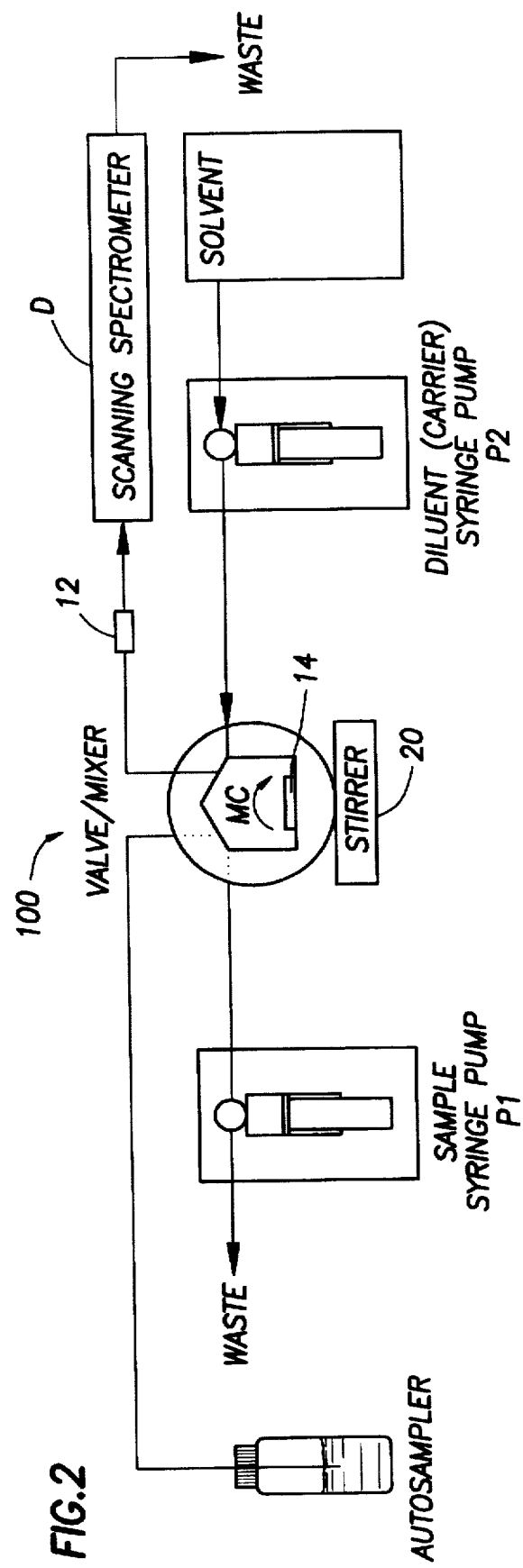
FIG. 2 is a detailed schematic of the flow injection system.
Figure 3A:
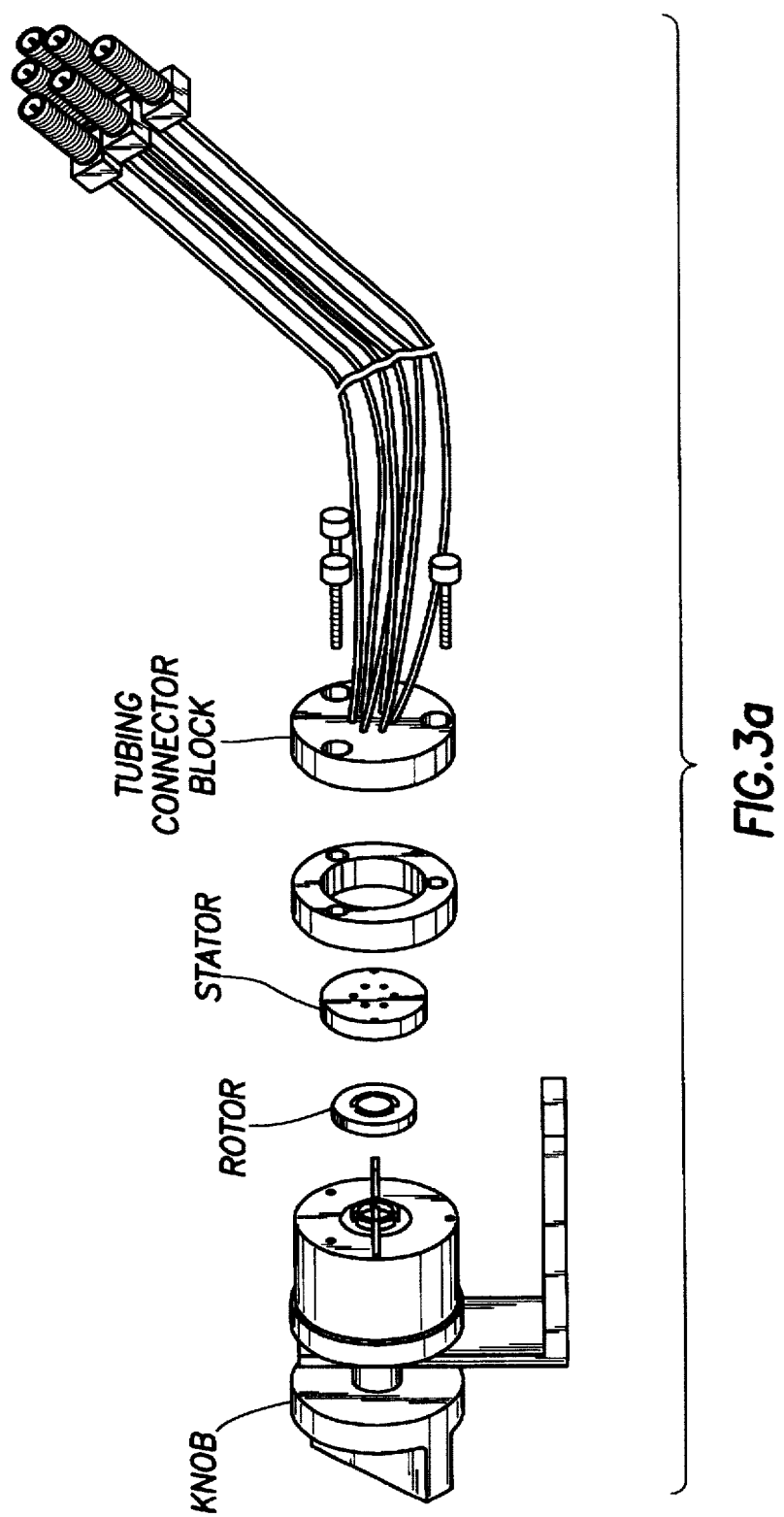
FIG. 3a is an exploded isometric view of the commercial valve which was modified for the invention.
Figure 3B:
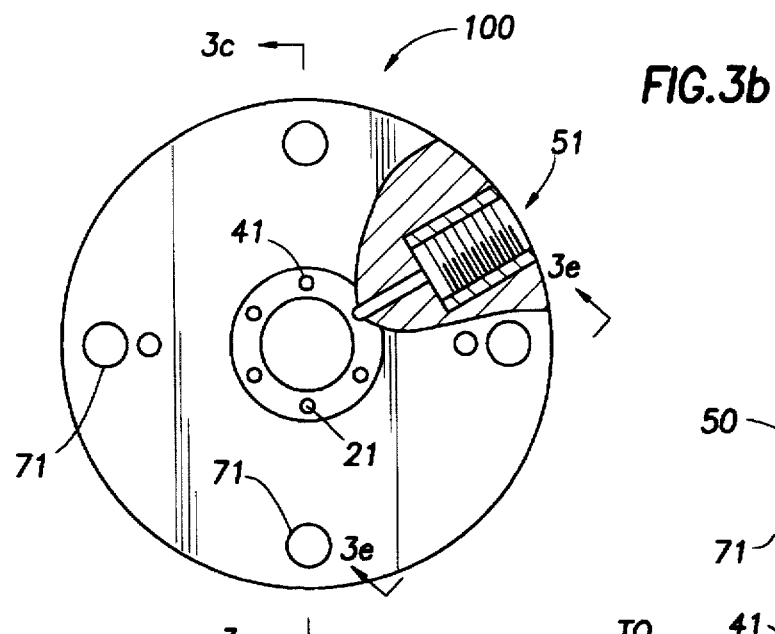
Figure 3C:
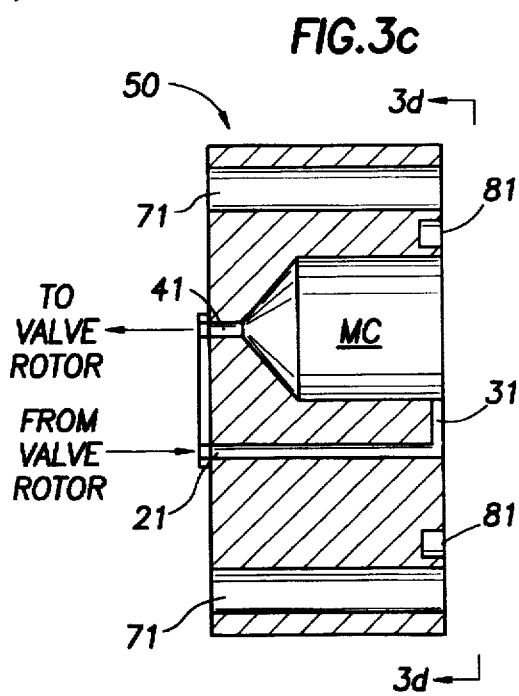
FIG. 3c is a sectional view of the mixer block of FIG. 3b taken along the line 3c—3c of FIG. 3b with the base plate removed.
Figure 3D:
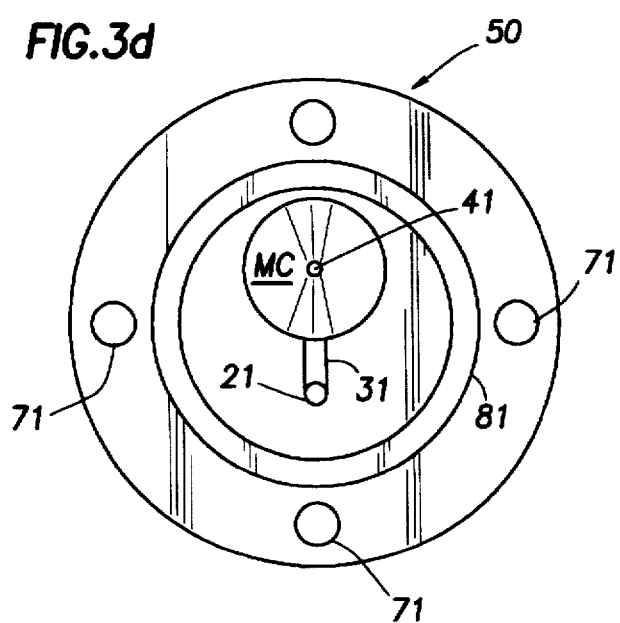
FIG. 3d is a bottom view of the mixer block taken in the direction of line 3d—3d of FIG. 3c.
Figure 3E:
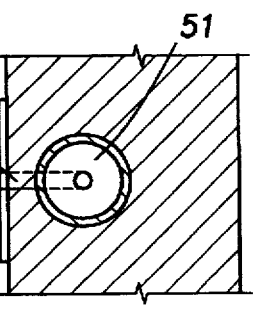
FIG. 3e is a view taken along line 3e—3e of FIG. 3b.

The manifold or flow injection system of the preferred embodiment is shown in FIG. 2. This shows how two syringe pumps can be used: one P1 (sample pump)for drawing a sample from an autosampler vial to fill the mixing chamber MC which is incorporated into a valve (and designated as valve/mixer 100), the other P2 (carrier pump) for flushing the sample out of the chamber MC through the scanning spectrophotometer or detector D, producing the required gradient. The system comprises autosampler (Gilson, 222x1), two syringe pumps (Gilson, 401 diluters), a modified injection valve (Valco) incorporating a mixing (gradient) chamber (described in detail with reference to FIG. 3) and stirrer motor 20 (Thermo Separations Products), and a fast-scanning high-resolution spectrophotometer D (Focus 2000, Thermo Separation Products) fitted internally with a 1 mm pathlength flowcell (Sapphire Engineering). These components are connected by open thermoplastic polymer tubing such as polytetrafluoroethylene (PTFE) or polyetheretherketone (PEEK) except between the valve/mixer 100 and the spectrophotometer cell, where a 4 cm single bead string reactor tube 12 (Dionex) is used. The valve/mixer 100 (shown in FIG. 2) comprises a two-part block (FIGS. 3c and d forming the mixer block 50 and FIGS. 3f and g forming the base plate 61), which replaces the tubing connector block in a Valco C10 series valve (shown in FIG. 3a), with a cylindrical chamber (MC) drilled into it. The two-part block was made of KEL-F® (registered trademark of The 3M Corporation) material. The "roof" of this chamber MC is conical to prevent air bubbles from becoming trapped in the chamber. Fluid enters the chamber MC by passing down from the valve rotor (FIG. 3a) through a channel 21 drilled parallel to the chamber and across to the chamber in a channel 31 engraved into the bottom surface of the mixer block 50. Fluid exits the chamber MC upwards from the top of the mixer block 50 (FIG. 3c) through the valve/mixer exit channel 41 and returns to the valve rotor completing the plumbing normally consisting of a sample loop. The other four channels 51 connect to the valve rotor and allow connection of the chamber MC, by threaded connection, to the sample inlet and outlet lines (when the valve is switched to the FILL position) or to the solvent inlet and outlet/spectrophotometer lines (when the valve is switched to the FLUSH position). A magnetic stirrer block 14 (Baxter/VWR#S8314-22) is inserted into the chamber MC nearly filling it to leave about 350 µl of mixing volume. The chamber is closed, and channel 31 completed, by the base plate 61 (FIG. 3f) which is held in place by brass bolts passing through all the chamber components via holes 71 and into the valve body (FIG. 3b and 3c), replacing the original bolts. The assembly is sealed by an "O"-ring (not shown) in groove 81 (FIG. 3c) machined into the mixer block 50. Stalling of the stirrer block 14 is reduced by a small knib 91 on the base plate 61 (FIG. 3f) which acts as a pivot on which the block 14 rotates. Switching of the valve is achieved using a Valco actuator (not shown) mounted on top of the valve unit (replacing the knob shown in FIG. 3a) and stirring, by a Thermo Separation Products stirrer motor 20 mounted using the adapter 30 (shown in FIGS. 3h, i and j) under the base plate 61 with the center of rotation of the stirrer motor 20 on the same axis as the chamber (MC). The adapter 30 is attached to the stirrer motor 20 via countersunk screws through holes 10 and the chamber assembly is held in the adapter 30 by gripping with grub screws through threaded holes 11.

Procedure

A laboratory must be able to handle samples ranging from light solvents to pitches and, for the flow injection (FI) method, a liquid sample is required. The robot is still used for making stock solutions of the samples; however, a less concentrated stock is used.

Once a satisfactory solution is obtained, usually by robot, the robot rack of stock solutions (still highly concentrated) is removed and placed in the autosampler. The control/calculation software has been written to enable manual entry of these solution concentrations or direct reading of the file created by the robot. Once all the relevant information has been entered into the computer (and saved as an "aromatic sample information" (.asi) file, a range of sample vials can be selected for dilution and scanning by the FI system.

Flow-Injection Dilution

In this system, use of a well-defined concentration gradient produces a function where concentration is a function of time. Although this approach to dilution for a known species has been demonstrated in a number of other instances, it is believed there is no prior demonstration of the use of a scanning or multiwavelength instrument with automatic characterization of the system and for obtaining poorly characterized (unknown) spectra. Multiwavelength instruments have been used, but only for known component analysis with calibration. In each of the previous gradient dilution systems, there has been the need to characterize the manifold in order to ensure accuracy. The software used in this system, coupled with the multiwavelength detector, negates the need for this characterization by using the data obtained. This allows changes to be made in the manifold such as flow-rate, tubing dimensions, sample and mixing chamber volume and flow-cell volume without affecting the precision or accuracy of the dilutions obtained. It should be noted that there is always some variation in the flowrate delivered by a pump and this system automatically accounts for that, producing more precise and accurate measures of dilution. Modification of a commercial valve FIG. 3a) such that it incorporates a mixing chamber MC in the mixer block 50 was also achieved as described above. This enables the sample to be flushed from the mixing chamber with the minimum of dispersion, which would distort the profile, and also simplifies the mechanical components required.

Figure 4:
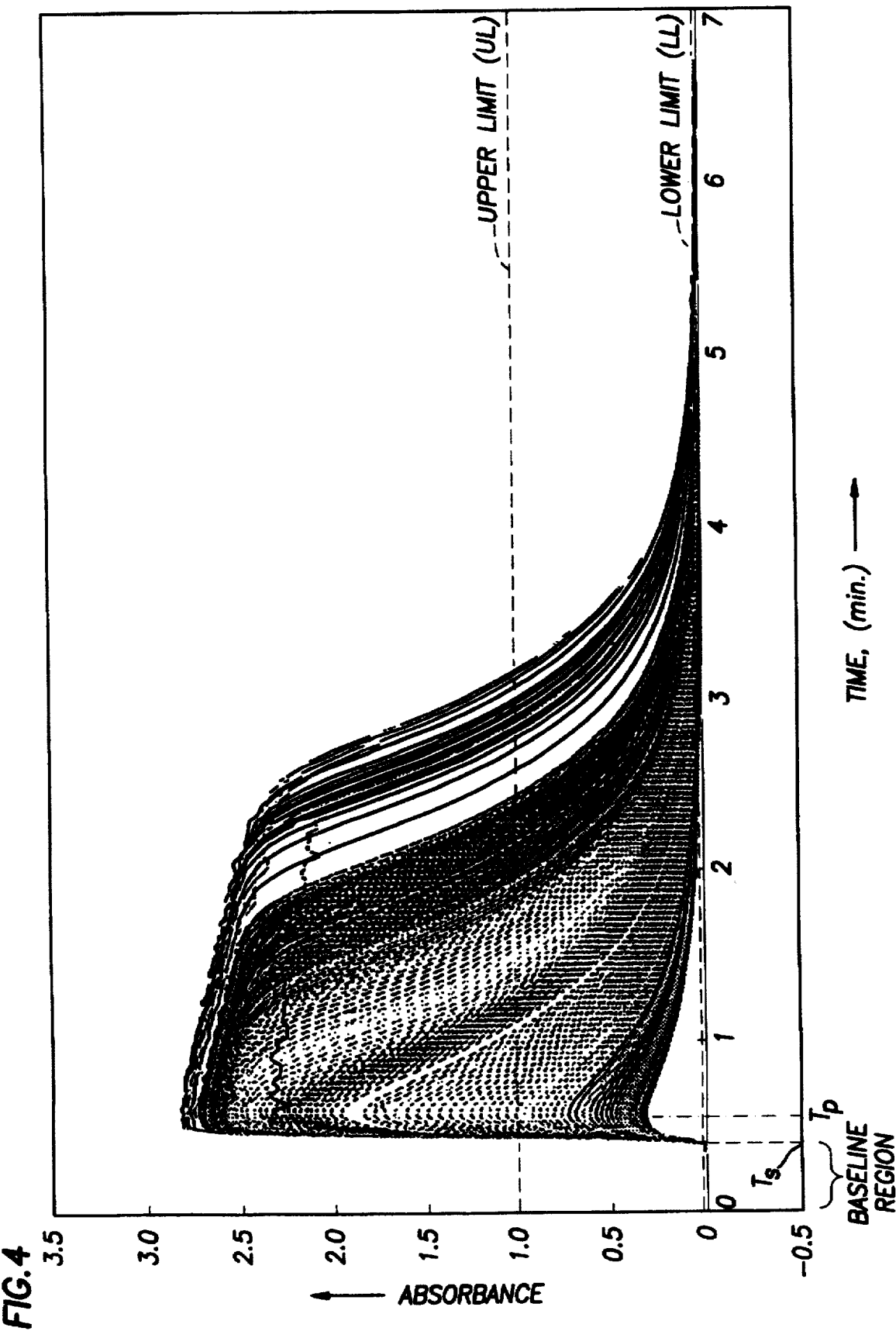
FIG. 4 is a plot of typical data obtained in an absorbance vs. time format for all wavelengths collected.

Once the system is started, the solvent (carrier) syringe P2 flushes the manifold with fresh solvent identical to that used by the robot for dissolution of the samples. This ensures that a correct baseline value is obtained. Then the mixing chamber MC is filled with the sample. Scanning is then started and the solvent is then pumped through the spectrophotometer D, bypassing the chamber MC, at 0.54 ml·min$^{-1}$ for 15 seconds before the valve switches the chamber MC into the flow path. This allows time for the baseline to be recorded before the valve is switched to FLUSH and the sample flows to the spectrophotometer D. The first portion of sample to arrive at the flowcell (in D) is diluted only by residual solvent in the single bead string reactor 12 and quickly (<3 seconds) rises to the undiluted concentration. This is followed by a sample of decreasing concentration as solvent flows into the mixing chamber MC and through the spectrophotometer D. After seven minutes, the concentration remaining in the system is negligible. As this stream of sample with changing concentration flows through the spectrophotometer, it is scanned from 190 to 375 nm to produce data as represented in FIG. 4. The process of injection/dilution/scanning is repeated three times for each vial before the next sample is analyzed. All three runs are recorded on graphs similar to FIG. 4.

Data Analysis

This procedure allows the parameters affecting dilution of flowrate and volume of mixing chamber, to be calculated directly from data obtained from samples, without characterizing or calibrating the manifold. In the instant invention, the characteristic property of the sample which is dependent on concentration and which is monitored during the exponential dilution, is absorbance, but other properties may be monitored.

The relationship between concentration and time for an exponential dilution chamber is well defined and common in fluid mechanics textbooks. Beer's law states that the optical absorbance is proportional to concentration and, for this procedure, Beer's law is considered to hold between absorbances of 0.0 and 1.0 (the linear range of the instrument), enabling us to use the concentration-time relationship for the gradient using absorbance or concentration interchangeably. The exponential dilution equation is $$C_m = C_i e^{-ut/V} \quad (1)$$

where $C_m$ is the original concentration of the stock, $C_i$ the concentration at time t, the time after the concentration begins to decrease, u the flowrate and V the volume of the mixing chamber.

Equation (1) can be rearranged and converted to the logarithmic form $$\ln C_i = (u/V)t + \ln C_m \quad (2)$$

Figure 5A:
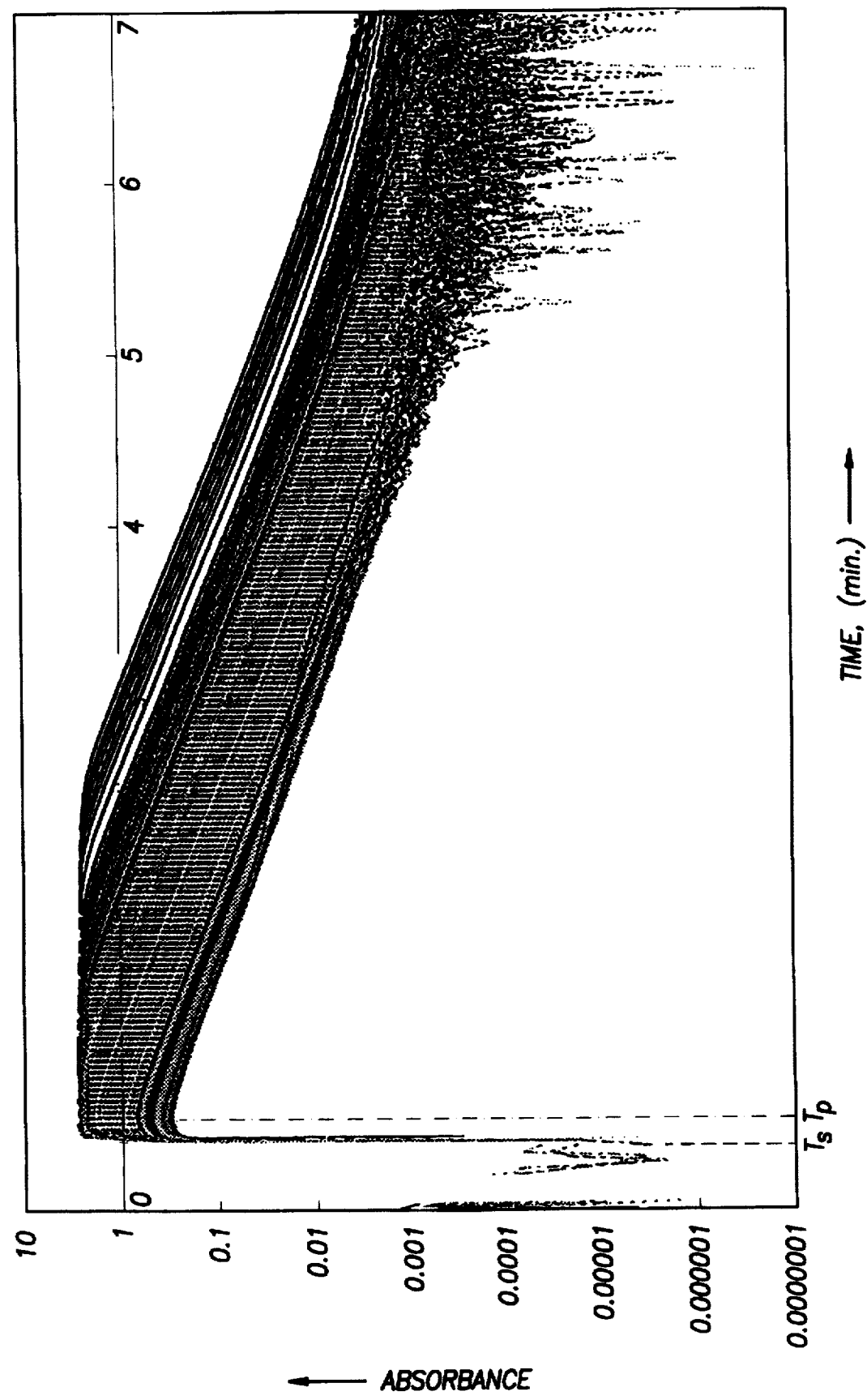
FIG. 5a shows a plot of the data from FIG. 4 plotted on a logarithmic absorbance axis vs. time.

FIG. 5a shows a plot of the data from FIG. 4 plotted on a logarithmic absorbance axis versus time which indicates the linearity of this data. The increase in noise below 0.001 is due to imprecisions in measurement and the lack of data resolution. The moment of injection is shown at $T_s$.

Before performing any data manipulation, any small baseline offset is subtracted from all the data for each wavelength. This improves linearity at the low absorbance levels. A straight line L is then fitted to the linear portion of the log data (as seen in FIG. 5b) and the slope of Equation (2), u/V found. However, the first part of the decay is distorted due to the finite length of tubing between the solvent inlet to the valve and the chamber, and data, offset from $T_p$, is used. During the regression process, outliers in the data are discarded using the method of Barnett (Barnett, V., in Statistical Methods and The Improvement of Data Quality, edited by Tommy Wright, pages 153–160, Academic Press, Inc., 1983) which helps eliminate any spikes in the data and excludes the curved extremes of the gradients which are distorted by dispersion in the system and by data resolution. A number of ways of determining the start of the decay curve ($T_p$) were tried and the best was found to be, as shown in FIG. 5b, by intersecting the line L fitted to the decay curve with the level of the peak maxima, for those peaks where the absorbance did not go off-scale. The values found are averaged for three to five wavelengths. Once the start of the decay ($T_p$) and the individual slopes (u/V) have been found, the slopes obtained by linear regression from all but the shortest wavelength data are averaged for later use. Most spectrophotometers show their worst performance at the shorter wavelengths and for the Focus instrument, the slope at 190 nm was not as consistent as those above 190 nm.

Because the spectrophotometer takes a finite time to scan from 190 to 375 nm (about 1.5 seconds), some correction must be applied to the gradient start time for each wavelength, depending on the time offset between the wavelength of interest and the wavelengths used to find $T_p$. Once the corrected start times and mean slope, u/V, of the gradients have been determined, time values where the absorbance (or concentration $C_i$) is less than or equal to 0.8 are found for each wavelength. The difference between this time and the start of the gradient is calculated to give t. The original absorbance (or concentration $C_m$) can then be determined by substitution of these values into Equation (2). This yields an absorbance value for each wavelength, i.e., a spectrum. As three injections are performed for each vial, three spectra (FIG. 4) are generated per vial.

Figure 7:
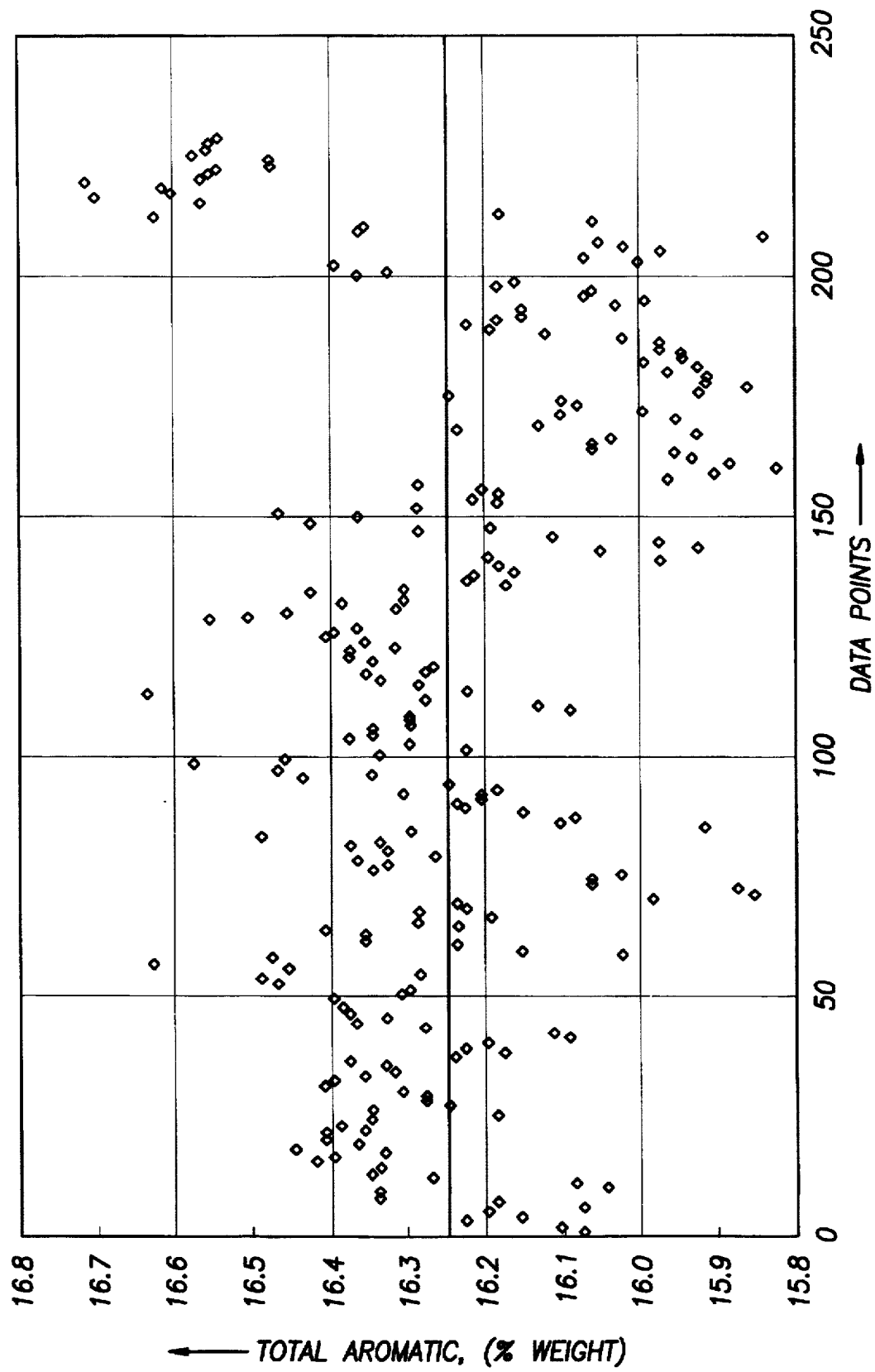
FIG. 7 shows a plot of the total aromatics obtained from the spectra produced by the invention, for the quality assurance sample for a number of analyses.

The spectra thus obtained using this inventive process may then be used to estimate the aromatic concentration in the samples. Because of the generation of three spectra per vial, some precision data can be generated for the dilution process (excluding that of the robot reflected in the differences between duplicate vials). We have found that, despite the logarithmic function used in the calculations, we can achieve precisions between 0.1 and 2.0% relative for each and total aromatics. Usually better than 1% is obtained. Examples of output are shown in FIG. 6a and can be compared to results obtained using the prior serial dilution process as shown in FIG. 6b. FIG. 7 shows a plot of the total aromatics for the quality assurance sample QA for a number of analyses. Table 1 presents an analysis of the data shown in FIG. 7.

TABLE 1

| | |
|---|---|
| Mean | 16.25035242 |
| Standard Error | 0.012392748 |
| Median | 16.28 |
| Standard Deviation | 0.186715578 |

TABLE 1-continued

| | |
|---|---|
| Sample Variance | 0.034862707 |
| Kurtosis | −0.416161801 |
| Skewness | −0.082994843 |
| Range | 0.89 |
| Minimum | 15.83 |
| Maximum | 16.72 |
| Sum | 3688.83 |
| Count | 227 |
| Confidence Level (95.0%) | 0.024420106 |

The software consists of a number of components and may be run on a 486 computer running Windows. UV main coordinates the launching of all the other components. First, an .asi file is created from sample information supplied by the user and generated by the robot, if used. The number of vials and a coded name is then displayed and a range of vials to be run can be selected. Initially, the DETECTOR program supplied by Thermo Separation Products is launched. (This program monitors, but it does not save, data, until started by a contact closure on the Detector D.) Next, the AUTOSAMPLER program (APPENDIX A) is launched. This program controls the mixer motor and valve, the syringe pumps, the autosampler probe and a contact closure for the detector. First, the solvent is flushed through the system and the mixer started. Next, the valve rotor is set to FILL and a sample is drawn in, filling the mixing chamber and then the diluent solvent pump P2 is started. The contact closure that starts the detector is then momentarily closed which initiates collection of data. After sufficient time to read the baseline has passed, the valve is switched to FLUSH which starts the gradient dilution process. After seven minutes, the solvent pump P2 is refilled, the valve returned to the FILL position, and the process repeated, either for a repeat of each sample for three replicates, or for the next sample until all the vials in the range have been run. Once all the vials have been run in triplicate, the AUTOSAMPLER and DETECTOR programs terminate and the data files generated are renamed to the coded name shown in UV main, since the DETECTOR program just generates sequential files. Next the program for obtaining spectra and chemical composition is launched, which itself launches a file conversion program supplied by Thermo Separation Products, converting the binary file format (bff) to ASCII format. Other programs may be used, for example, the REDUCE program supplied with the DETECTOR program. This ASCII file is then read and the following procedure is then performed.

PROGRAM PROCEDURES FOR OBTAINING SPECTRA

This processing program has the following key components: Main, RunInfo, Vial, Injection, Calculation, ReadFile, and Report.

Figure 8A:
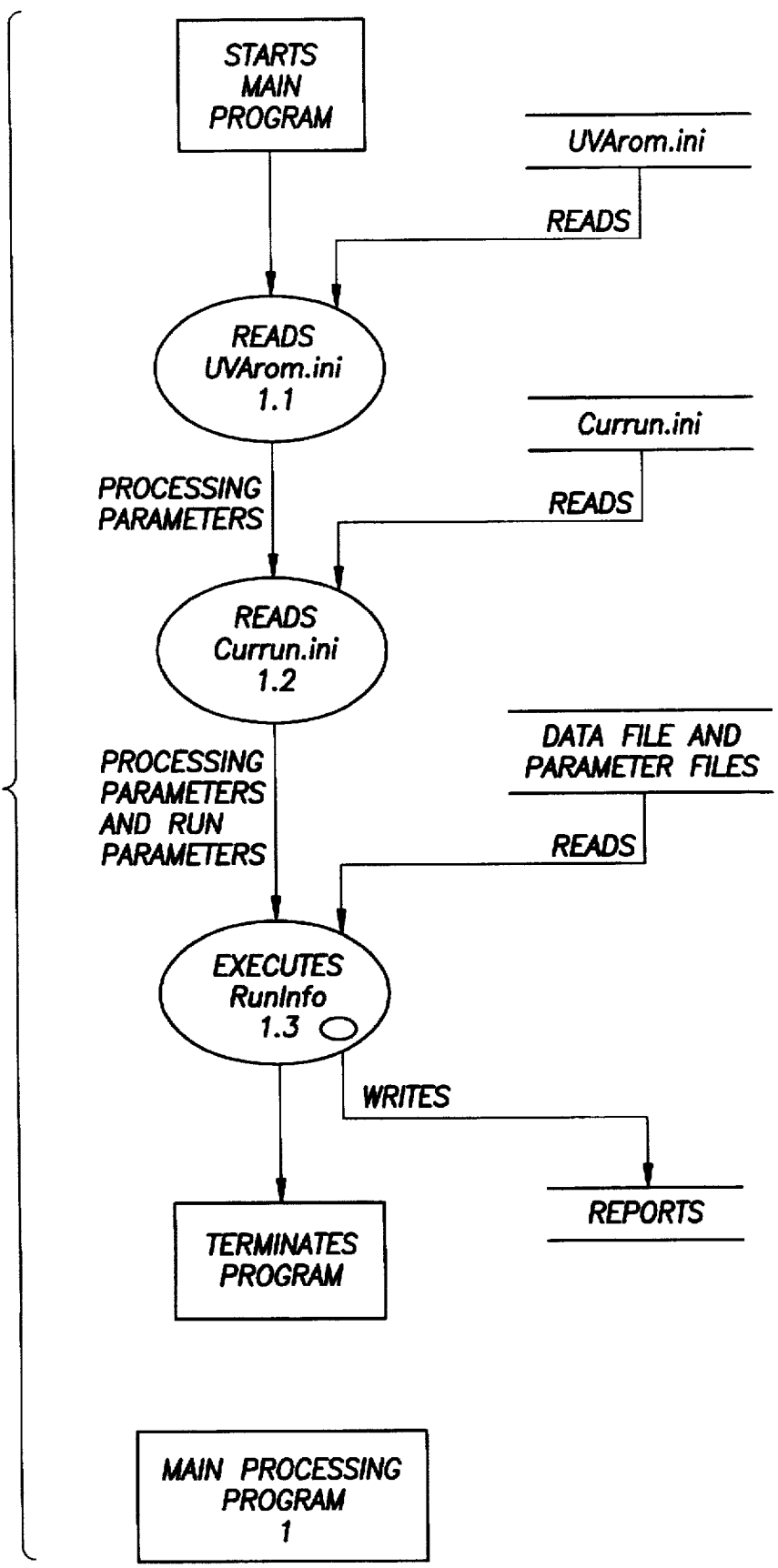

Main Module (FIG. 8a)
Purpose: This module controls the initiation and termination of the program. It is the main control loop. Upon initiation by the user or other programs, the Main Module performs the following:

1. Reads the uvarom.ini file to get the default processing parameters given and described in APPENDIX B.
2. Reads the currrun.ini file to get the name of the run file to process.
3. Activates the RunInfo Module and waits for its completion.
4. Responds to user's input via the mouse or keyboard.
5. Terminates the program upon completion of the RunInfo Module or user request.

RunInfo Module (FIG. 8b) Purpose: This module controls the processing of a series of data files specified by the run file. Upon initiation by the Main Module, the RunInfo Module performs the following:

1. Reads the content of the specified run file to get the list of data files to be processed.
2. Initializes storage for the first vial.
3. Sequentially goes through the list of data files. If the vial number of the current data file is different from the vial number of the preceding data file, activates the report generation for the preceding vial and initializes storage for the new vial.
4. Activates the Injection Module to process the data file.
5. Calculates statistics and prints a report.
6. Returns control to the Main Module when all the files specified in the run file are processed.

Vial Module (Within the Run Info module, FIG. 8b) Purpose: This module provides storage, status information and calculates vial statistics for each vial. Each vial should have one to three injections. The calculated spectrum and results from each injection are stored in the Vial Module. The statistics such as mean, variance and percent error of the three injections are computed in this module.

Injection Module (FIG. 8c) Purpose: This module performs computation of the data. Upon initiation by the RunInfo Module, the Injection Module performs the following:

1. Activates the ReadFile Module to read the data file.
2. Determines the baseline region and beginning rise point $T_s$ of the absorptive spectrum at 200 nm. Searching from time zero on the spectrum at 200 nm, $T_s$ is determined as the point that precedes the first point that has an absorbance above a preset level (SV in APPENDIX B). The baseline region is defined as the middle thirty percent of points between time zero and $T_s$.
3. Applies baseline correction by subtracting the average of the baseline region (FIG. 4) from the entire spectrum.
4. Step 3 is repeated for all the wavelengths. A baseline average is computed for each wavelength using the baseline region determined in step 2.
5. $T_p$, where the decay curve starts (t=0 Equation (1)), is determined by locating the peak maximum of wavelengths that have their absorbances within the defined range between HV and SV in Appendix B. Interpolation is used to gain better accuracy. $T_p$ is calculated as the average of the $T_p$ found in all the wavelengths that have valid absorbances.
6. Data are then truncated if specified by the processing parameter limits in the .ini file (APPENDIX B) and the precision of the data is improved by removal of outliers by the method of Barnett as previously defined.

Figure 8B:
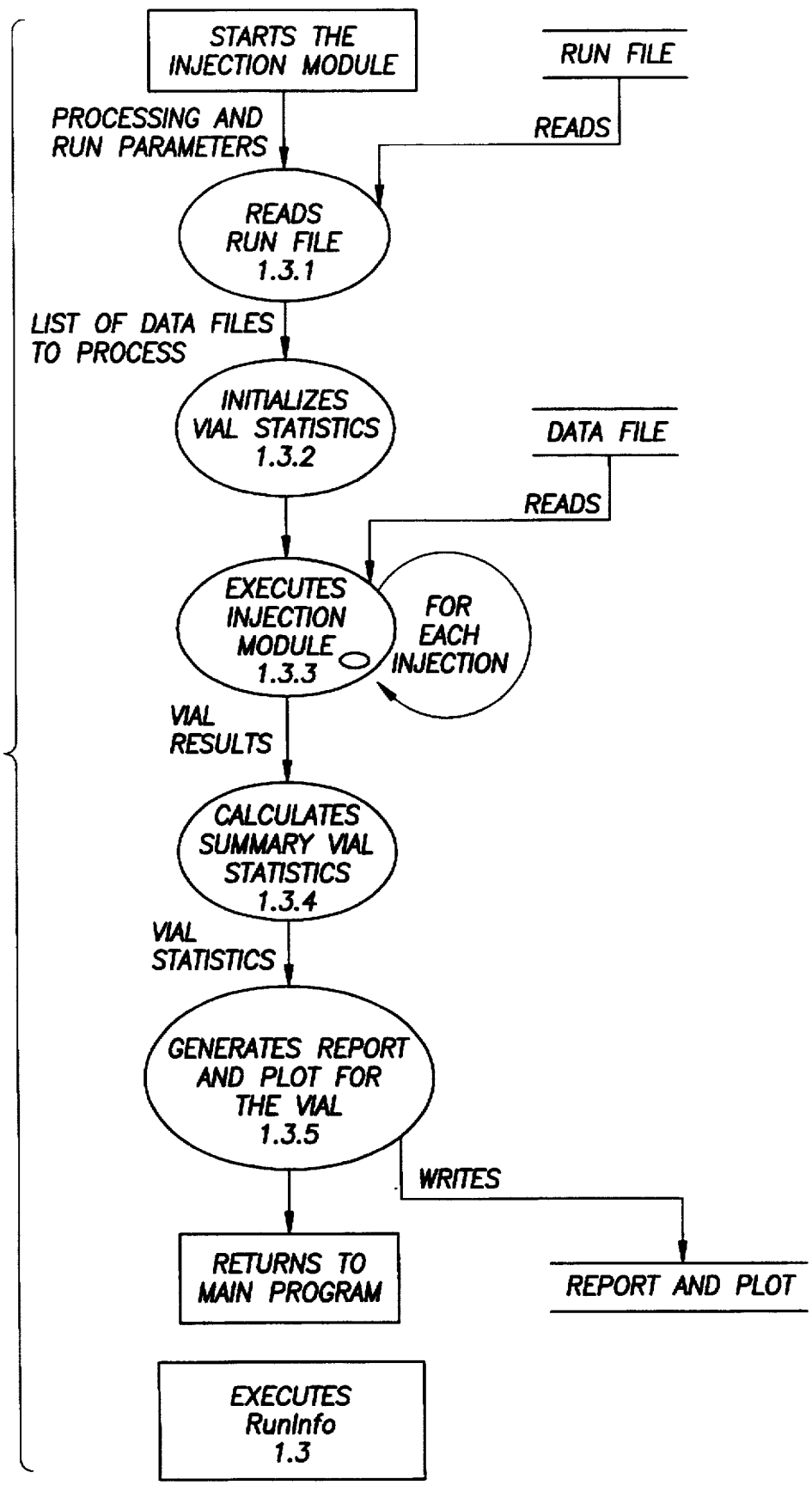

Determining $C_m$ (FIG. 8d)
7. $C_m$, the absorbance values at $T_p$ for each wavelength are computed. $C_m$ is determined based on the following procedure:

a. For each wavelength, the optimal position to perform the computation is determined using the following criteria:
      i. The absorbance has to be within the lower (LL) and upper limits (UL) FIG. 4) specified by the processing parameters. Short wavelengths can have different limits from the long wavelengths (see APPENDIX B).
      ii. The optimal position cannot be within two data points of data spikes found by the method of Barnett.
      iii. The optimal position is the data point that satisfies i and ii and has its absorbance closest to the upper limit UL.
      iv. The data point is after $T_p$.

b. Seventeen data points around the optimal position that are not contaminated by data spikes are used to compute the linear slope and intercept for the wavelength. For the regression, the y vector is the natural log value of the absorbances. The x vector is the corresponding time minus $T_p$.

c. The optimal time $T_i$ is determined as the time for the ninth point (middle) of the seventeen points used in the regression.

d. The optimal absorbance $C_i$ is interpolated at $T_i$ using the equation $$C_i = \exp(\text{slope}*(T_i-T_p) + \text{intercept}).$$

This relates directly to Equation (2) in that here slope is $-1/v$, $T_i-T_p$ is t and intercept is $\ln C_m$.

In this case, slope and intercept were found in step b.

e. The average of the slopes for wavelengths from 200 nm to 320 nm is computed.

f. $T_p$ is then corrected for the finite time it takes to perform a scan by the following equation:

$$T_p\text{corrected} = (\ln(T_p) - \ln(C_i))/\text{Average slope} + T_i + dT_i \text{ is computed}$$

where $dT_i = T.i/n$ and T is the time for a single scan, i is the index (or the order number of the wavelength) and n is the number of wavelengths read.

g. $T_p$ corrected is computed for all the wavelengths that have valid $T_p$ determined in step 5.

h. True $T_p$ is the average of all the $T_p$ corrected in step 7g.

i. $C_m$ values for all wavelengths are then calculated.

For wavelengths that have absorbances above the lower limit, $C_m$ is computed by the equation $$C_m = C_i * \exp(-\text{Average slope}*(T_i + dT_i - \text{True } T_p))$$

where $dT_i$ corrects $T_i$ for scanning offset as it did for $T_p$.

This is the program form of Equation (1). For wavelengths that do not have absorbances above the lower limit, the absorbance at $T_p$ is assigned to $C_m$. This produces the spectrum to which the invention relates. Then the original absorbances of the samples, i.e., before being diluted into a stock solution, are calculated by division of these $C_m$ values by the product of the concentration of the stock and the pathlength of the detector $C_m$ original $= C_m/$(Concentration * PathLength).

8. The Calculation Module is activated to determine the chemical components in the sample.

9. Returns control to the RunInfo Module.

Figure 8C:
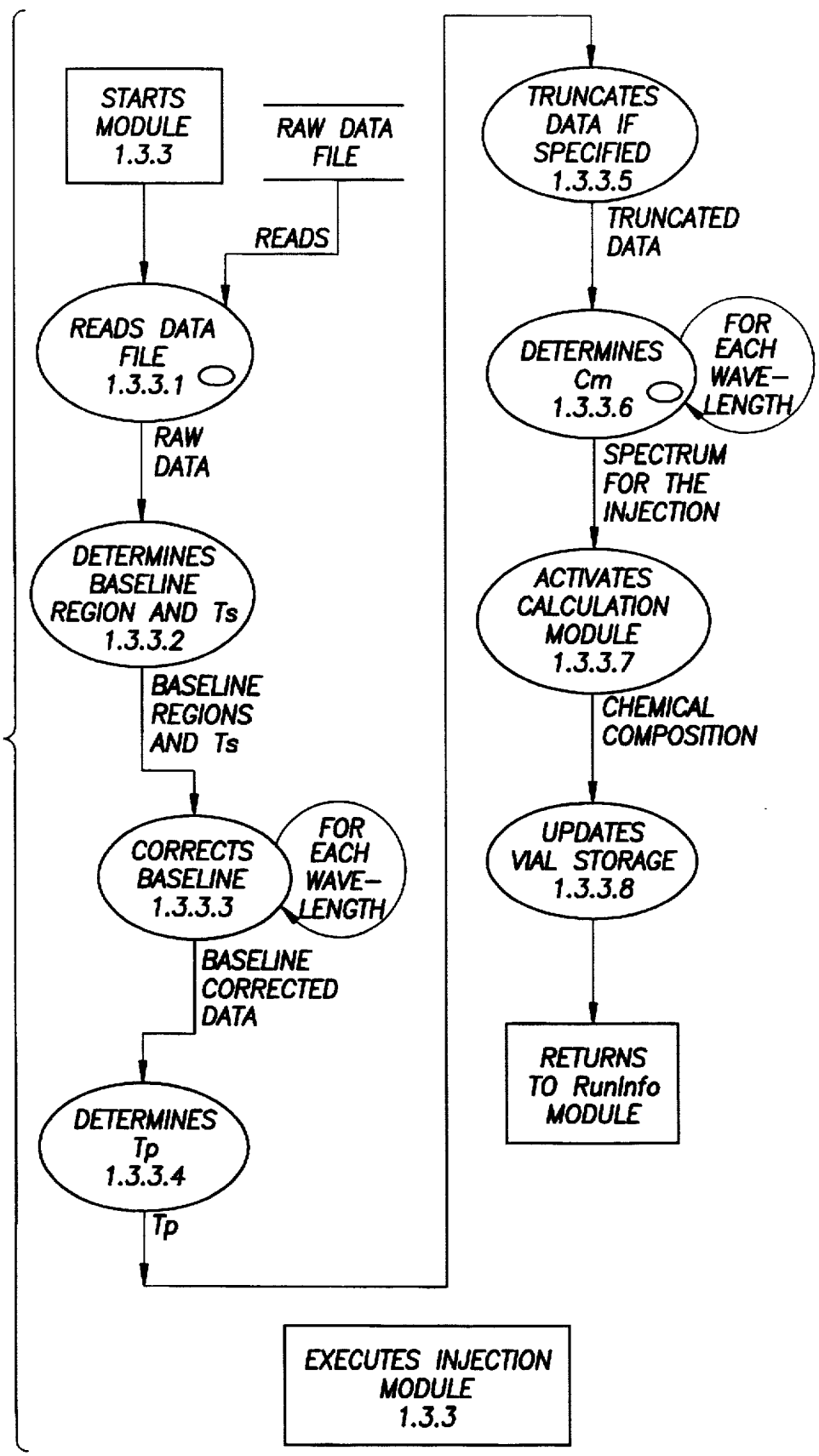
Figure 8D:
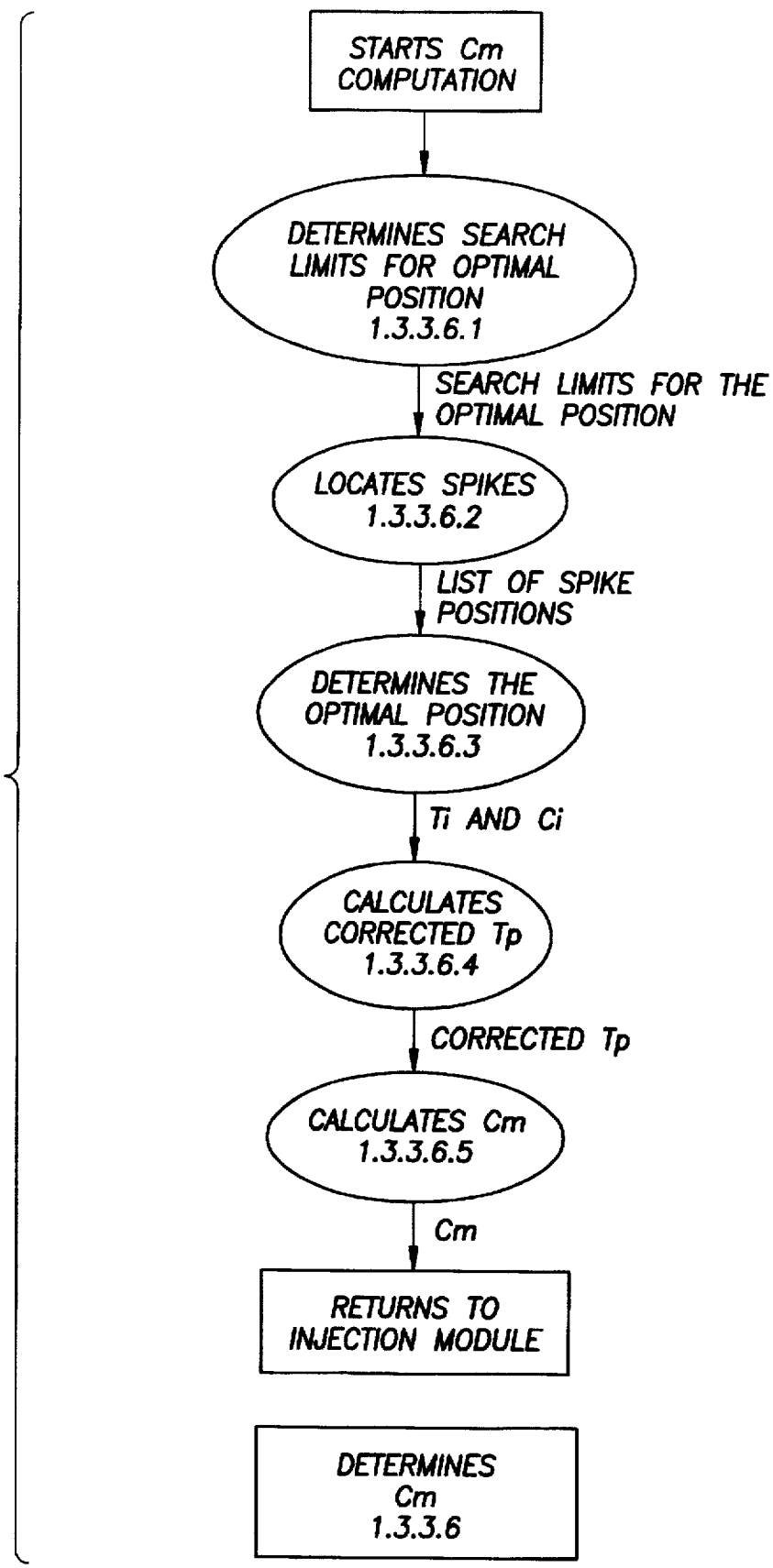

Calculation Module (Within the Injection Module. FIG. 8c)
Purpose: This module quantifies the chemical components detected in the sample. The module returns control to the Injection Module upon completion.

ReadFile Module (FIG. 8e) Purpose: This module is responsible for the reading of the data file. Upon initiation by the Injection Module, the ReadFile Module performs the following:

1. The module reads an ASCII data file. If the ASCII file is not present, the module calls the routine that converts a bff file to an ASCII file.

2. The data is read into memory.

3. Returns control to the Injection Module.

Report Module (Within the RunInfo Module. FIG. 8b) Purpose: This module is responsible for the generation of the report for the analysis. Upon initiation by the RunInfo Module, the Report Module performs the following:

1. Generates a single report for each vial.

2. Returns control to the RunInfo Module.

The data flow diagrams (FIGS. 8a–e) were generated using a drawing package by VISIO Technical.

Autosampler Control

The AUTOSAMPLER program (APPENDIX A) contains explanatory comments. It coordinates the pumps, valves, mixer and detector as described above. A Pharmacia pump was used initially and rudimentary routines remain in the program for its control, but that pump has been replaced in this embodiment by the Gilson pump.

CONCLUSION

FIG. 6a shows results obtained using the invention to obtain UV spectra of a hydrocarbon sample and to then deduce the aromatic content from the spectrum obtained. These results are compared to FIG. 6b which shows the results obtained using serial dilution with a robot and scanning the solutions to generate the spectrum. In FIG. 7, quality assurance data for one sample is also presented which show the repeatability of the system over a number of runs. Table 1 presents an analysis of the data shown in FIG. 7.

The exponential dilution obtained using a well-stirred chamber allows spectra (and concentrations) to be obtained from a wide range of original concentrations when most of the spectral absorbance is too great to be measured conventionally. Any imprecision introduced by using the logarithmic function can be countered by careful choice of equipment and by building routines into the software that eliminate bad data points. With the instant system, within-run precisions better than 1% are routinely obtained and much of the imprecision appears to be due to the initial robot dilutions and to the samples themselves. Between-run precision is comparable to that obtained using serial robot dilution.

Because this system requires some portion of the spectrum to be "on-scale," the stock dilution injected may have to be more dilute than those used to make dilutions for the prior method. However, for most samples, the absorbance around 360 nm is on scale for stocks containing about 0.1 g per 20 ml of solvent.

This invention is used for obtaining spectra for concentrated samples using a UV spectrophotometer for subsequent calculation of their aromatic hydrocarbon content. It is envisioned that the dilution system will have wide application to process and laboratory analysis and that this system could be developed into an on-line analyzer for automated control of units (such as catalytic-cracking units) by measurement of aromatic content of feeds. Other uses of this system include calibration for multi-element or multi-species analysis of concentrated samples using other spectroscopies (e.g., NMR, XRF, ICP, etc.) and single species determination with reference to a second spectral wavelength/line (e.g., in fluorescence, absorbance, etc.) or using an internal standard.

APPENDIX A

{*****************************************************************}

5   AUTOSAMPLER PROGRAM (written in Turbo PASCAL using Gilson's library routines)

{set things up}

```
        USES Samplib, Crt;
10      VAR V1, V2, row, col, inj, inc,VP, VL, dv:integer;
        FileName : string[60];
        dummystr : string[3];
        f : text;
        {******}
15
        {******}
        BEGIN
        DefineSampler(1, 10, 123, 0, M222);
        Define401(1, 0, 10000, 10000000);
20      Define401(2, 2, 10000, 100000000);
        CheckConfiguration;
        InitializeSystem;
        SetSensitivity(1, 1);

25
        {************************Start Method***********************}
        ClrEol;
        Writeln(' UVaromatics program for 222 xl autosampler ');
        ClrEol;
30      ClrEol;
        {start mixer}
        SetElectricalContact(1, 1, ON);
        {refresh solvent in carrier pump}
        dil401valve(2,reservoir);
35      dil401asp(2,10000,20);
        dil401valve(2,needle);
        dil401disp(2,10000,20);
        dil401valve(2,reservoir);
        dil401asp(2,1000,20);
40      dil401valve(2,needle);
        dil401disp(2,1000,20);
        dil401valve(2,reservoir);
        dil401asp(2,1000,20);
        dil401valve(2,needle);
```

```
         dil401disp(2,1000,20);
         dil401valve(2,reservoir);
         dil401asp(2,10000,5);
         dil401valve(2,needle);
 5       {wait for lamp to warm up}
         WaitTime(5);
         SetElectricalContact(1, 6, OFF);
         {run pump}
         WaitTime(1.5);
10       Writeln(' ');
         ClrEol;
         {read purge, load, starting vial, ending vial from file}
         FileName := 'c:\uv\auuvarom.dat';
         assign(f, FileName);
15       Reset(f);
         Readln( f, dummystr, VP);
         writeln( 'VP=', VP);
         Readln( f, dummystr, VL);
         writeln( 'VL=', VL);
20       Readln(f, dummystr, V1);
         writeln( 'V1=', V1);
         Readln(f, dummystr, V2 );
         writeln( 'V2=', V2);
         close(f);
25       writeln('inc=',inc);
         FOR row := 0 To 4 DO
         BEGIN
         FOR col := 0 To 7 DO
         BEGIN
30       {increment till vial number is achieved}
         inc:=inc+1;
         {test to see if all vials have been done}
         IF inc>(v2) THEN
         BEGIN
35       MoveToHome(1);
         AbortApplication;
         END;
         {check to see if increment is at first vial}
         IF inc>=v1 THEN
40       BEGIN
         ClrEol;
         writeln('sampling from vial   ', inc);
         SetVial(1, 9, 9, 9);
         {pause pump while sample purges}
```

```
        SetElectricalContact(1, 3, OFF);
        {move valve to inject to bypass air from chamber}
        SetElectricalContact(1, 2, ON);
        {aspirate air and purge sample volume}
 5      movetoxyz(1, 53+(col*38),86+(row*38),300,noseek,wait);
        dil401valve(1,needle);
        dil401asp(1,200,5);
        wait401(1);
        DV:=DV+200;
10      movetoxyz(1, 53+(col*38),86+(row*38),-112,noseek,wait);
        dil401asp(1,VP,5);
        wait401(1);
        DV:=DV+vp;
        dil401valve(1,reservoir);
15      dil401disp(1,dv,20);
        dv:=0;
        dil401valve(1,needle);
        ClrEol;
        Writeln('initial load done');
20      {unpause pump}
        SetElectricalContact(1, 3, ON);
        {prepare to inject 3 samples}
        FOR inj := 1 To 3 DO
        BEGIN
25      {move valve to fill}
        SetElectricalContact(1, 2, OFF);
        {aspirate sample}
        dil401asp(1,VL,4);
        wait401(1);
30      DV:=DV+vl;
        ClrEol;
        Writeln('sample loaded');
        {start carrier flow for 7+ minutes i.e wait 1 + wait 2}
        dil401disp(2,3900,0.543);
35      {start detector}
        SetElectricalContact(1, 4, PULSE);
        {wait 1}
        WaitTime(0.4);
        {inject sample}
40      SetElectricalContact(1, 2, ON);
        dil401valve(1,reservoir);
        dil401disp(1,dv,20);
        dv:=0;
        dil401valve(1,needle);
```

```
        {flush old sample out of line with air and or wait}
        IF inj=3 THEN
        BEGIN
        MoveZ(1,0,1000);
   5    dil401asp(1,1000,10);
        DV:=1000;
        dil401valve(1, Reservoir);
        dil401disp(1,DV,40);
        dv:=0;
  10    {wait 2}
        WaitTime(6.6);
        END
        ELSE
        BEGIN
  15    {wait 2}
        WaitTime(6.6);
        END;
        ClrEol;
        ClrEol;
  20    {ensure line is flushed}
        dil401disp(2,500,3);
        {refill carrier pump}
        dil401valve(2,reservoir);
        dil401asp(2,4400,4);
  25    dil401valve(2,needle);
        WaitTime(0.1);
        {change Pharmacia pump direction if connected}
        SetElectricalContact(1, 5, PULSE);
        END;
  30    END;
        END;
        END;

MoveToHome(1);
  35    WaitTime(4);
        {empty pumps}
        init401(1);
        init401(2);
        {stop Pharmacia pump}
  40    SetElectricalContact(1, 3, OFF);
        {stop mixer}
        SetElectricalContact(1, 1, off);
        end.
```

APPENDIX B

*date created or modified* c:\uv\detector\bff2exl.exe *location of conversion utility*

Scale Upper Limit *The upper absorbance limit for finding times of peak maxima (HV)*

1.5

Scale Lower limit *The lower limit below which data is not used for finding peak maxima (SV)*

.2

1=save result file, 0=no *An option that allows the results to be saved*

0

1=print result, 0=no *An option that allows the results to be printed*

1

Longest wavelength used *Where the wavelength range can be set*

375

1=print Diagnostics, 0=no *An option allowing parameters to be printed (during development)*

0

Fit Upper Limit(Lamda<300) *The upper limit of linearity of absorbance* (UL)

1

Fit Lower limit *below which data is too noisy to be used (LL)*

.08

Concentration *no longer used (data now read from robot file)*

11

PathLength *of the flowcell in the detector*

.1

Run file used for automation *no longer used (now generated by UVMain program)* c:\uv\data\MR010850\MR010850.run

Fudge factor *A factor used during program development to adjust the data to be comparable to conventionally obtained data. Now equal to 1, hence does not change the data.*

1

Flag, 1=Yes to all message box, 0=stop to response *allows program development/error checking*

1

High WL limit (for fit upper limit) *allowed division of the spectrum into 2 wavelenth (WL) areas with different limits. Limits are now equal hence no effect.*

300

High WL fit upper limit(Lamda>=300* (UL)

1

Baseline correction flag, 1=BC,0=No BC *Allows baseline correction to be deselected*

1

$T_pT_s$ factor *applies a small offset from the peak maximum to where the program starts to regress the slopes. Now has little effect due to the method of Barnett being applied to the data.*

1.2

FlagSvSpectra, >0 Save spectra in ASCII file. *No longer used.*

0

T_pLeftOffset, data point from peak to start fit. *No longer used.*

1

T_pRightOffset, data point from peak to start fit. *No longer used.*

2

SmoothPts, Number of points used for smoothing. *The number of points used in the regression*

17

MinSmoothPts, Min. no of points used for smoothing. *The minimum number of points for regression which must remain after the method of Barnett has been applied*

4

MinGoodNeeded, *Number of WLs for averaging the time of the peak maximum*

5

FlagDebug, 1=Generate a debug file, o.w.=no debug *Causes a file to be generated of parameters calculated in the procedure*

0

FlagDeleteASCII, 1=Delete ASCII file after processing. o.w=no *Allows the ASCII file generated by conversion of the bff file to be saved or deleted*

What is claimed is:

1. A dilution system for obtaining original concentrations of solutions by gradient dilution, without prior calibration of the dilution system or having prior knowledge of parameters on which concentration depends, comprising:

an injection valve for controlling fluid flow, said injection valve incorporating a chamber;

a first pump for pumping a sample of a concentrated solution through said valve and into said chamber;

a second pump for pumping a diluent through said valve and into said chamber at a constant flow rate;

means for continuously mixing said sample and said diluent within said chamber;

means for continuously diluting said sample with said diluent, thereby forming a solution having a continuously decreasing concentration-versus-time;

monitoring means for measuring a characteristic property of said sample which property is dependent on concentration, for continuously receiving said continuously decreasing concentration-versus-time solution from said chamber and continuously collecting data for determining said characteristic property of said solution;

means for determining the dilution parameter of the ratio of flow rate and chamber volume from said data; and means for calculating the original, undiluted concentration, or property related to concentration, of said concentrated solution using said parameter and said data.

2. The system according to claim 1 wherein a mixing chamber is used to produce said concentration-versus-time dependence for said solution.

3. The system according to claim 2 wherein said mixing chamber is a well-stirred tank.

4. The system according to claim 2 wherein said mixing chamber is an open tube.

5. The system according to claim 2 wherein said concentration-versus-time dependence is an exponential function.

6. The system according to claim 1 wherein said property monitored is optical absorbance.

7. The system according to claim 1 wherein said monitoring device is a scanning spectrophotometer.

8. The system according to claim 7 wherein said scanning spectrophotometer is a diode array spectrophotometer.

9. A method for obtaining a characteristic property of a concentrated solution by flow injection gradient dilution wherein said characteristic property is directly related to concentration, comprising the steps of:

providing a concentrated solution;

filling a chamber with a sample of said concentrated solution;

flowing a diluent into said chamber at a constant flow rate during a flowing period;

mixing the contents of said chamber during said flowing period;

moving the contents of said chamber from said chamber at said constant flow rate during said flowing period;

providing said flow to a means for monitoring said characteristic property related to concentration of said solution;

monitoring said characteristic property related to concentration of said flowing solution as a function of time;

recording said characteristic property related to concentration of said flowing solution as a function of time to produce a data set;

extracting a gradient feature, including the ratio of said flow rate and said chamber volume, from said data; and calculating the original, undiluted concentration, or property related to concentration, of said concentrated solution using said feature and said data.

10. The method of claim 9 wherein flow into and out of said chamber is constant during dilution.

* * * * *